(12) United States Patent
McKelvey

(10) Patent No.: US 12,742,766 B2
(45) Date of Patent: Sep. 22, 2026

(54) SYSTEM AND METHOD FOR MONITORING WATER QUALITY

(71) Applicant: OzGreen Energy Pty Ltd, Arundel (AU)

(72) Inventor: Len McKelvey, Arundel (AU)

(73) Assignee: Ozgreen Energy Pty Ltd (AU)

( * ) Notice: Subject to any disclaimer, the term of this patent is extended or adjusted under 35 U.S.C. 154(b) by 364 days.

(21) Appl. No.: 18/268,283

(22) PCT Filed: Dec. 17, 2021

(86) PCT No.: PCT/AU2021/051504
§ 371 (c)(1),
(2) Date: Jun. 19, 2023

(87) PCT Pub. No.: WO2022/126194
PCT Pub. Date: Jun. 23, 2022

(65) Prior Publication Data

US 2024/0118257 A1 Apr. 11, 2024

(30) Foreign Application Priority Data

Dec. 18, 2020 (AU) ................................ 2020904744

(51) Int. Cl.
*G01N 33/18* (2006.01)
*G01N 1/20* (2006.01)
*G08B 21/18* (2006.01)

(52) U.S. Cl.
CPC ............... *G01N 33/18* (2013.01); *G01N 1/20* (2013.01); *G08B 21/182* (2013.01)

(58) Field of Classification Search
CPC ......... G01N 33/18; G01N 1/20; G08B 21/182
See application file for complete search history.

(56) References Cited

U.S. PATENT DOCUMENTS 10,180,414 B2 1/2019 Clark et al.
2005/0065755 A1 3/2005 McCarter et al.
(Continued)

FOREIGN PATENT DOCUMENTS

CN 107884530 4/2018

OTHER PUBLICATIONS

International Preliminary Report on Patentability for Application No. PCT/AU2021/051504 dated Jan. 12, 2023.
(Continued)

*Primary Examiner* — David J Bolduc
(74) *Attorney, Agent, or Firm* — Tumey L.L.P.

(57) ABSTRACT

A water quality monitoring system for monitoring water quality in a water distribution network comprising a plurality of distribution lines for interconnecting a plurality of distribution lines with one or more nodes from which water is supplied into the distribution network, the system comprising: a plurality of water sampling sub-systems, each subsystem being arranged in fluid communication with a corresponding distribution line for obtaining water quality parameters from said corresponding distribution line, each subsystem comprising a communication module for communicating data related to a water quality parameter to a database over a communication network wherein each of the sub-systems are functionally linked with each other over the communication network to trigger simultaneous measurement of the water quality parameters. The system further comprises means to display a graph that provides a visual indication of the water quality.

10 Claims, 5 Drawing Sheets

(56) References Cited

U.S. PATENT DOCUMENTS

| | | | | |
|---|---|---|---|---|
| 2007/0219728 | A1 | 9/2007 | Papageorgiou et al. | |
| 2008/0178663 | A1* | 7/2008 | Yang | G01N 33/18 73/61.41 |
| 2016/0356755 | A1 | 12/2016 | Gifford et al. | |
| 2018/0202890 | A1* | 7/2018 | Mutch | G01M 3/28 |
| 2019/0257806 | A1* | 8/2019 | Page | G01N 33/18 |
| 2019/0270655 | A1* | 9/2019 | Jorden | C02F 1/56 |
| 2019/0297397 | A1 | 9/2019 | Fleishman | |
| 2020/0264151 | A1* | 8/2020 | Do Quang | G01N 33/18 |
| 2020/0340967 | A1 | 10/2020 | Jenkins | |
| 2021/0278092 | A1* | 9/2021 | Revilla | G01N 33/18 |
| 2021/0309539 | A1* | 10/2021 | Budampati | H04L 67/30 |
| 2021/0404907 | A1* | 12/2021 | Fung-A-Wing | G01F 15/005 |

OTHER PUBLICATIONS

Carminati, M. et al., “A Self-Powered Wireless Water Quality Sensing Network Enabling Smart Monitoring of Biological and Chemical Stability in Supply Systems”, Sensors, MDPI, Published: Feb. 19, 2020, <URL: https://www.mdpi.com/1424-8220/20/4/1125>.

International Search Report and Written Opinion for Application No. PCT/AU2021/051504 dated Mar. 3, 2022.

Saudi Authority for Intellectual Property Substantive Examination Report for Application No. 523441249 dated Dec. 26, 2024.

Huijun Zhao et al., “A Real-Time Water Quality Information Acquisition System for Wastewater Source Control”, Oct. 31, 2012, pp. 1-51, http://www.urbanwateralliance.org.au/publications/UWSRA-tr84.pdf.

D B Hart et al., “Canary Users Manual Version 4.3.2”, Sep. 2012, pp. 1-7.

* cited by examiner

SYSTEM AND METHOD FOR MONITORING WATER QUALITY

RELATED APPLICATIONS

The present application claims priority from Australian provisional application number 2020904744 filed 18 Dec. 2021, the content of which is hereby incorporated by reference in its entirety.

TECHNICAL FIELD

The present invention relates to a system and method for monitoring water quality.

BACKGROUND

Any references to methods, apparatus or documents of the prior art are not to be taken as constituting any evidence or admission that they formed, or form part of the common general knowledge.

Drinking water in many drinking water distribution systems is currently monitored by manually taking infrequent water samples at a limited number of locations. Samples then undergo laboratory analysis for a list of contaminants. From the time of contamination, the turnaround time for a positive detection could range from days to weeks, depending on the type of contaminant and the accessibility to laboratory services. Therefore, there is a need to provide real time water quality monitoring.

In real time water quality monitoring, considerable difficulties have been experienced in collecting and processing of measurements from remote sensors in a way that facilitates quick and accurate interpretation of the measurements by a human operator. The Inventors have discerned that these difficulties arise mainly because of problems associated with correlating measurements with actual conditions over time periods of interest. Moreover, when a large number of water sampling devices are used for constant water quality monitoring, large volumes of water quality related data need to be processed and analysed to provide any meaningful inference to personnel who are responsible for monitoring water quality. The applicant's previous invention, published as PCT/AU2020/050073 (incorporated herein by reference) provides a water quality monitoring device that enables real time water quality monitoring. However, when a large number of water quality monitoring devices are reporting water quality results back to the server it becomes incredibly difficult, if not impossible for a person to process the data in real time and provide any meaningful information to operators. Therefore, there is at least a need to provide an improved method and system that addresses some of the shortcoming of the prior art and existing technologies.

SUMMARY OF INVENTION

In some of the following statements summarising the invention, where features are mentioned item numbers from the Figures will be provided as an example of the feature for the convenience of the reader. It will be understood that such examples are purely exemplary and are not intended to be limiting of the features.

In an aspect, the invention provides a water quality monitoring system for monitoring water quality in a water distribution network 80, comprising a plurality of distribution lines 90 interconnecting one or more nodes from which water is supplied into the distribution network, the system comprising:

a plurality of water sampling sub-systems (100), each sub-system (100) being arranged in fluid communication with a corresponding distribution line (90) for obtaining data related to water quality parameters from said corresponding distribution line (90), each sub-system (100) comprising a communication module (110) for communicating the data related to at least one water quality parameter to a database (42) over a communication network (29) wherein each of the sub-systems (100) are functionally linked with each other over the communication network to allow all of the sub-systems in the corresponding distribution lines to be triggered to perform simultaneous measurements of the water quality parameters in a measurement event (213);

a remotely located server computer (33) in communication with said plurality of water sampling sub-systems (100), said server computer (33) including a processor (35) and a non-volatile memory device (47), wherein said processor (35) is operable to perform the steps of: retrieving the data from the database (42) to determine:

- a maximum measured value (202) for the water parameter from a set of water parameter values measured by each sub-system in each measurement event (213);
- a minimum measured value (204) for the water parameter from the set of water parameter values measured by each sub-system in each measurement event (213);
- an average measured value (205) for the water parameter computed by calculating an average of all the measured values of the water parameter in the set;
- the memory device comprising executable instructions to display a graph (207) that includes a first axis (209) to indicate the maximum measured value (202), the minimum measured value (204) and the average value (205) for each measurement event (213) and a second axis (211) to indicate a time period over which a plurality of said measurement events have occurred thereby provide a visual indication of water quality.

In an embodiment, the processor (35) for the remotely located server computer 33 is operable to determine a range (206) of the measured values of the water quality parameter by computing a difference between the maximum measured value (202) and the minimum measured value (204) and wherein the memory device comprises executable instructions (48) to indicate the range (206) of the measured values on the first axis (209).

In an embodiment, the system further comprises a user input interface (43,44) in communication with the processor (35) for controlling operation of the functionally linked water sampling sub-systems (100) and initiating one or more measurement events (213).

In an embodiment, each sub-system (100) is configured to measure one or more of the following: (a) pressure: (b) transient pressure; (c) temperature of water; (d) pH of water; (e) oxidation reduction potential (ORP); (f) Conductivity (Ec); (g) Free Chlorine concentration, (h) Turbidity.

In an embodiment, the memory device (47) comprises executable instructions (48) to additionally indicate if a maximum measured value exceeds a pre-determined maximum limit value and/or if a minimum measured value is less than a predetermined minimum limit value for the water quality parameter.

In an embodiment, the memory device comprises executable instructions to compute a difference between the average value of each measurement and the maximum measured value for each measurement and process said difference in accordance with one or more predetermined rules to provide an indication of unexpected changes in water quality.

In an embodiment, the memory device comprises executable instructions to compute a difference between the average value of each measurement and the minimum measured value for each measurement and process said difference in accordance with one or more predetermined rules to provide an indication of unexpected changes in water quality.

In another aspect, the invention provides a method of monitoring water quality in a water distribution network (80) comprising a plurality of distribution lines (90) interconnecting one or more nodes from which water is supplied into the water distribution network (80), the method comprising:

arranging a plurality of water sampling sub-systems (100) in fluid communication with a corresponding distribution line (90) and obtaining water quality parameters from said corresponding distribution line wherein each of the sub-systems (100) are functionally linked with each other over the communication network to allow all of the sub-systems in the corresponding distribution lines to be triggered to perform simultaneous measurements of the water quality parameters in a measurement event (213);

communicating data, via a communication module (110) of each of the the water sampling sub-systems, related to a water quality parameter to a database (42) over a communication network (29);

arranging a remotely located server computer (33) and retrieving data from the database (42), said server computer (33) including a processor (35) and a non-volatile memory device (47) and operating the processor (35) to process the retrieved data to determine:

a maximum measured value (202) for the water parameter from a set of water parameter values measured by each sub-system in each measurement event (213);

a minimum measured value (204) for the water parameter from the set of water parameter values measured by each sub-system in each measurement event (213);

an average measured value (205) for the water parameter computed by calculating an average of all the measured values of the water parameter in the set; and arranging a display device (33) in communication with the processor (35) and the memory device (47) to display a graph (207) that includes a first axis (209) to indicate the maximum measured value (202), the minimum measured value (204) and the average value (205) for each measurement event (213) and a second axis (211) to indicate a time period over which a plurality of said measurement events (213) have occurred to thereby provide a visual indication of water quality.

In an embodiment, the method further comprises the step of determining a range of the measured values of the water quality parameter by computing the difference between the maximum measured value and the minimum measured value and wherein the memory device comprises executable instructions to indicate the range of the measured values on the first axis.

In an embodiment, the method further comprises the step of displaying pre-determined maximum and minimum limit values for the water quality parameter on the display device.

In an embodiment, the method further comprises the step of computing a difference between the average value of each measurement and the maximum measured value for each measurement and processing said difference in accordance with one or more predetermined rules to provide an indication of unexpected changes in water quality.

In an embodiment, the method further comprises the step of computing a difference between the average value of each measurement and the minimum measured value for each measurement and process said difference in accordance with one or more predetermined rules to provide an indication of unexpected changes in water quality.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
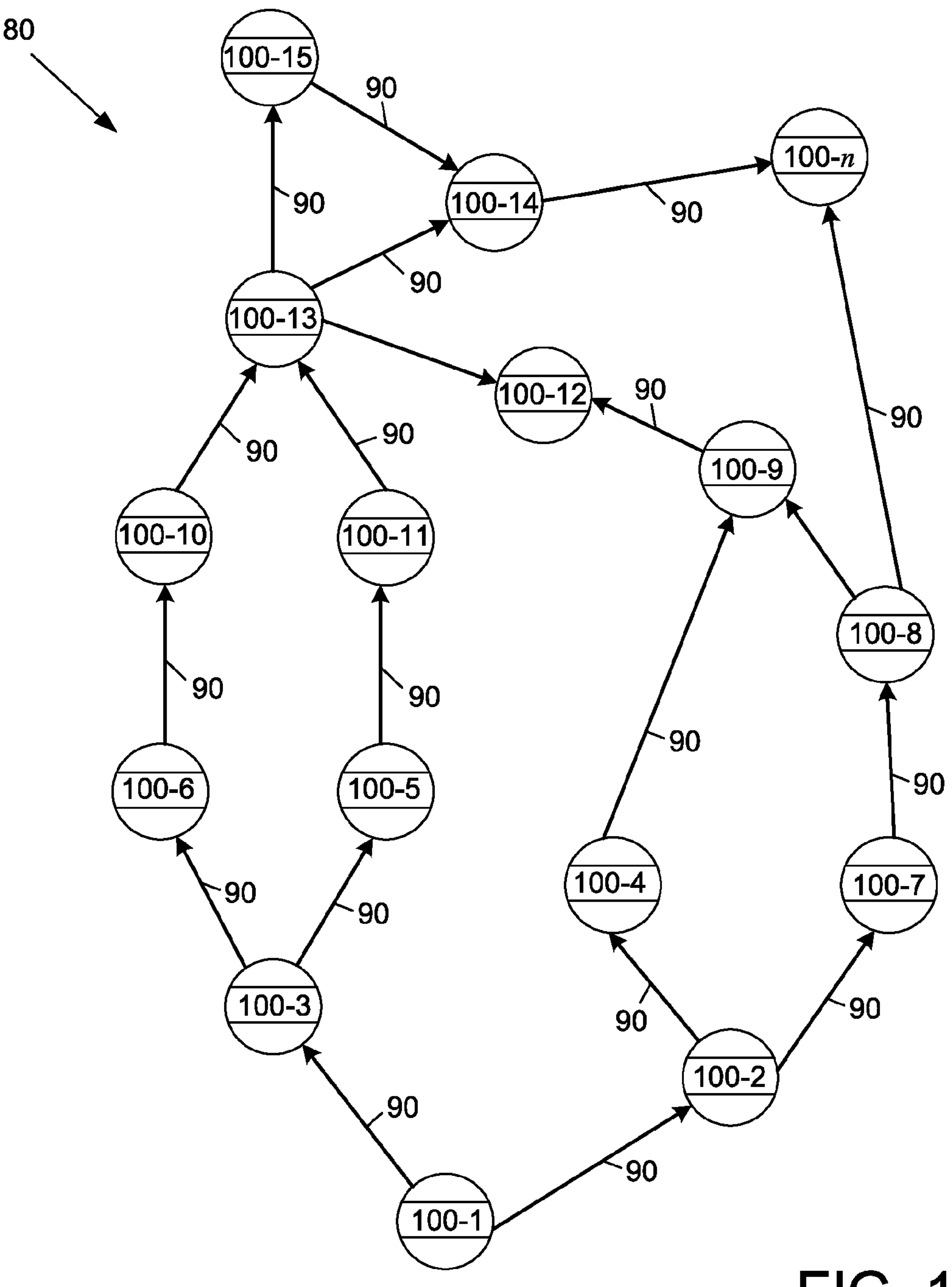
FIG. 1 is a line diagram of a water distribution network utilising a plurality of water sampling sub-systems 100 in corresponding distribution lines in a water distribution network.

FIG. 1 illustrates a line diagram of a water distribution network 80 comprising a plurality of distribution lines 90 (arrows show the direction of flow of water) interconnecting one or more nodes from which water is supplied into the distribution network where n water sampling sub-systems 100-1, . . . , **100-*n* generally denoted by 100 have been arranged in fluid communication with a corresponding at least one distribution line 90**.

In at least some embodiments, each water sampling sub-system 100 may be provided in the form of a pit lid mounted water sampling and testing system described in PCT/AU2020/050073. Each lid mounted water sampling sub-system 100 may be arranged to be in fluid communication with a corresponding distribution line 90 for obtaining water quality parameters from the corresponding distribution line. Each water sub-system comprises a communication module 110 for communicating data related to water-quality parameters from each sub-system to a database 150 over a communication network 29, such as a wireless communication network (internet in the preferred embodiment).

Figure 2:
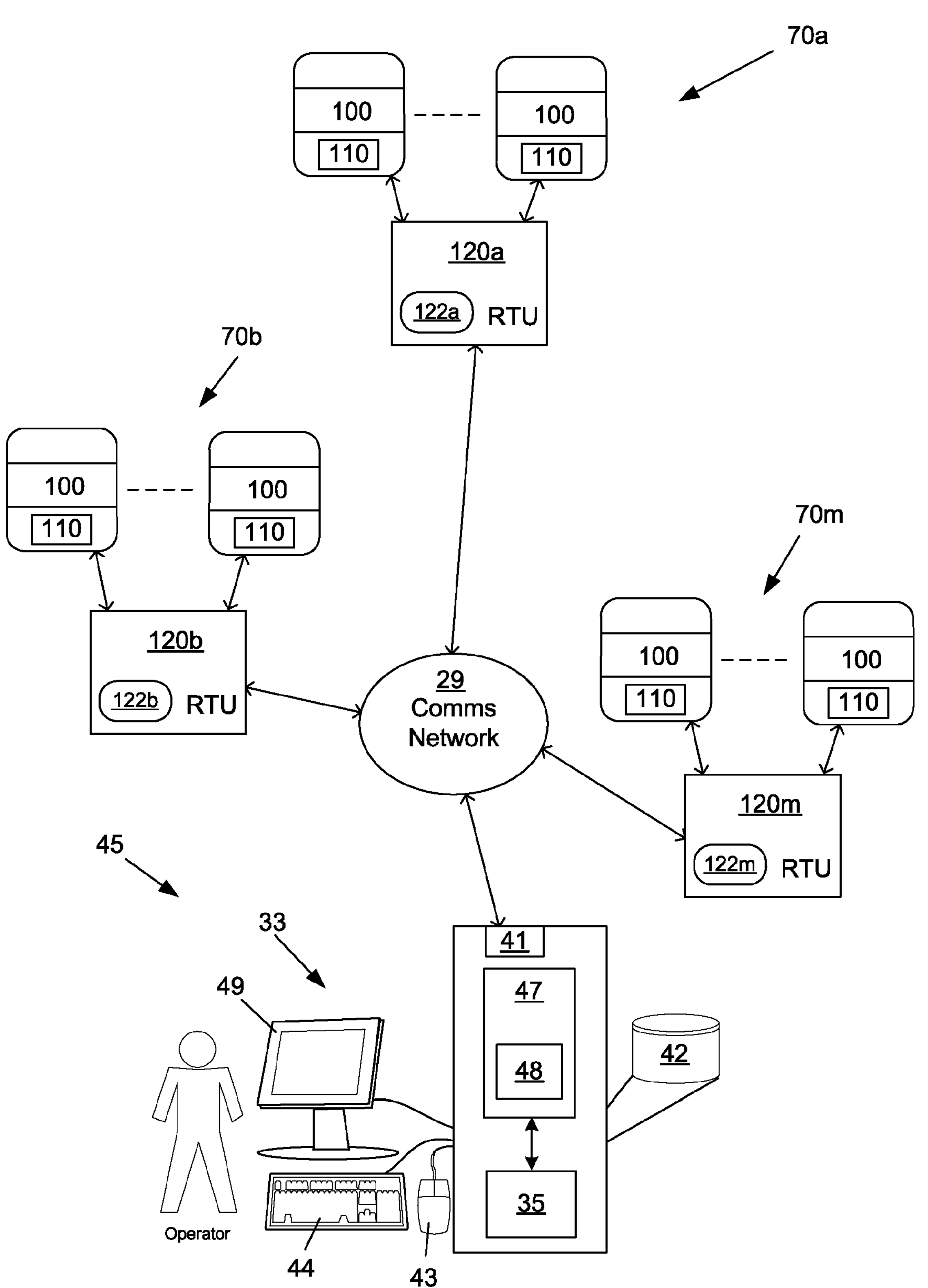
FIG. 2 is a box diagram illustrating various functional elements of a water quality monitoring system in accordance with a preferred embodiment.

As illustrated in FIG. 2, the sampling sub-systems 100 are grouped into a number of groups wherein sampling sub-systems of each group are in data communication with a common Remote Terminal Unit (RTU) 120. A RTU is a microprocessor-based device that monitors and controls field devices, that then connects to plant control systems. The term "RTU" as used herein is meant to encompass functionally equivalent devices, for example suitably programmed programmable logic controllers (PLC) with network accessibility and data storage capability.

Figure 4:
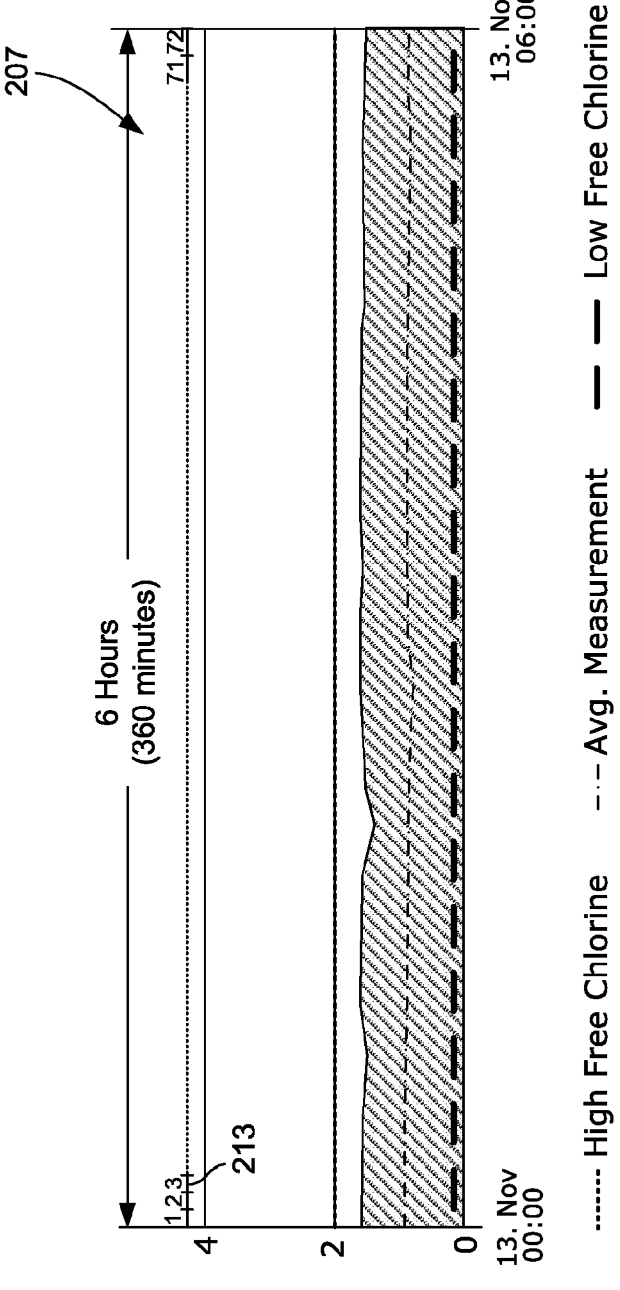
FIG. 4 is a second visualisation produced by the system of the preferred embodiment.

For example, in FIG. 2 groups **70*a*, 70*b*, . . . , 70*m* of sampling sub-systems 100 are shown wherein the sampling sub-systems 100 of group 70*a* are each in data communication with RTU 120*a*, the sampling sub-systems 100 of group 70***b* are each in data communication with RTU 120*b*, and so on, up to group 70*m* whose sensor sub-systems 100 are each in data communication with RTU 120*m*. Each of the sensor-subsystems 100 is a network device and is able to monitor a reference time signal, for example a signal from an internet accessible clock. Each sampling sub-system 100 assumes an idle mode in which it listens for a wake-up call from the RTU in its group. Upon receiving the wake up call the sampling sub-system readies itself to make measurements of parameters at a time specified by the RTU. Since all the sub-systems monitor a common reference time signal they are effectively functionally linked with each other over the communication network to allow them to be triggered for simultaneous measurement of the water quality parameters by all the of the functionally linked sub-systems 100 in the corresponding distribution lines in a measurement event. For example, measurement events 213 may be triggered at five minute intervals as shown in FIG. 4 where 72 measurement events are shown over the course of a six hour period from 00:00 hours on 13 November to 06:00 hours on the same day. Each RTU includes a data logger 122*b* which stores measurement data from the sensor sub-assemblies 100 in the RTU's group. Measurement data from the RTU data loggers 122 is then transmitted via communication network 29 for storage in database 42. In other alternative embodiments, measurement events 213 may be triggered to be performed simultaneously within a certain time period or range of time whereby the measurement events 213 may not occur exactly at the same time but within a defined time period. For example, that time period may be defined to be a 5 minute period and all "simultaneous" measurements in an event would be undertaken during this specified time period.

A remotely located server computer 33 is arranged to be in communication with the plurality of water sampling sub-systems 100, said server computer including one or more processors (CPUs) 35 and a non-volatile memory device 47 such as a secondary storage hard drive or solid-state drive. The server 33 also includes usual componentry such as a mainboard that couples various modules together including a ROM containing a BIOS or UEFI for booting up the server prior to loading of an operating system, RAM, an operating system stored in the secondary storage, a communications module such as a network-interface-card and a graphics driver for interfacing between the CPU and a display device such as a flat screen monitor.

The processor 35 is configured by instructions comprising a program 48 stored in secondary storage 47 to be operable to perform the steps of: retrieving data from the database 42 to determine: a maximum measured value (My) (indicated as 202 in FIG. 3) for the water parameter from a set of water parameter values measured by each sub-system 100 in each measurement event 213; a minimum measured value (MN) (indicated as 204 in FIG. 3) for the water parameter from the set of water parameter values measured by each sub-system in each measurement event and an average measured value (Au) (indicated as 205 in FIG. 3) for the water parameters, which processor 35 computes by calculating an average of all the measured values of the water parameter in the set of water parameter values for each measurement event. In the preferred example, for every measurement event, 16 data points are recorded for each water sampling sub-system 100. Specifically, a range (indicated as 206 in FIG. 3) of the measured values (M R) of the water quality parameter is obtained by computing the difference between the maximum measured value (My) 202 and the minimum measured value (MN) 204.

Figure 3:
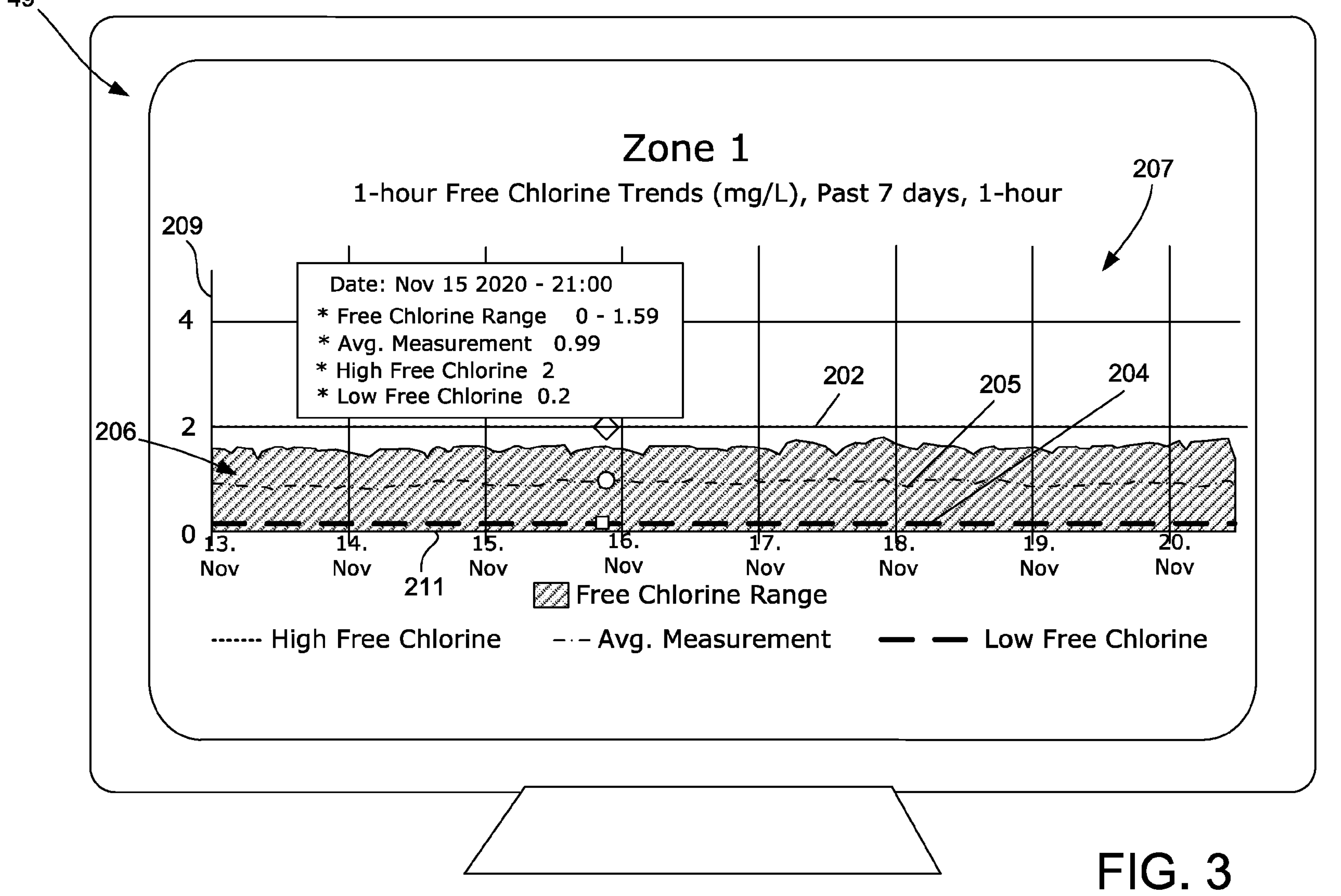
FIG. 3 is a first visualisation produced by the system of the preferred embodiment.

The memory device 47 stores executable instructions that comprise a program 48 that configure processor 35 to display a graph (indicated as 207 in FIG. 3, on a display device 49, that includes a first axis 209 to indicate the maximum measured value (My) 202, the minimum measured value (MN) 204 and/or the range 206 of the measured value (MR) and the average value (Av) 205 for each measurement event 213 (FIG. 4) and a second axis 209 to indicate a time period, e.g. from 00:00 Hrs on 13 November to 12:00 Hrs on 20 November in FIG. 3 over which a plurality of said measurement events 213 have occurred thereby providing a visual indication of water quality. The system and method described herein are used to transform data obtained by the inter-connected water sampling sub-systems 100 and visualization techniques are used for presenting a large volume of data in a manner that is more suitable and useful for quick evaluation and analysis by operators and supervising personnel.

Referring once again to FIG. 2, the processor 35 in combination with the memory device 47 and the display device 49 may be referred to as a data visualization device 45 in accordance with an embodiment. The data visualization device 45 may f include an input interface, e.g. keyboard 44 and mouse 43, an output interface such as display device 49, a communication interface such as modem 41 and may retrieve datasets (e.g. sets of measurement value data relating to water quality parameters) from the database 42. Fewer, different, and/or additional components may be incorporated into data visualization device 45.

An Input interface may provides an interface for receiving information from a user for entry into the data visualization device 45 as understood by those skilled in the art. Input interface may interface with various input technologies including, but not limited to, a keyboard, a mouse, a display, a track ball, a keypad, a microphone, one or more buttons, etc. to allow the user to enter information into data visualization device or to make selections presented in a user interface displayed on the display. The same interface may support both input interface and output interface. For example, a touch screen display supports user input and presents output to the user. The data visualization device 45 may have one or more input interfaces that use the same or a different input interface technology. The input interface technology further may be accessible by data visualization device through communication interface. The user input interface may also receive user input to trigger a measurement event. Specifically, each of the water sampling sub-systems 100 may be functionally linked to the processor 35 via the communication network 29 and RTUs 120 to actuate or trigger one or mare measurement events simultaneously in each of the sensor sub-assemblies 100.

An output interface may also be provided for outputting information for review by a user of data visualization device. For example, output interface may interface with various output technologies including, but not limited to, a display, a printer, etc. Data visualization device may have one or more output interfaces that use the same or a different output interface technology. The output interface technology further may be accessible by data visualization device through the communication interface.

The communication interface, e.g. interface 41, provides an interface for receiving and transmitting data between devices using various protocols, transmission technologies, and media as understood by those skilled in the art. Communication interface may support communication using various transmission media that may be wired and/or wireless. Data visualization device 45 may have one or more communication interfaces that use the same or a different communication interface technology. For example, data visualization device may support communication using an Ethernet port, a Bluetooth antenna, a telephone jack, a USB port, etc. Data and messages may be transferred between data visualization device and other computing devices using communication interfaces.

The memory device 47 is an electronic holding place or storage for information and instructions such as the instructions comprising program 48, so the information can be accessed by processor 35 as understood by those skilled in the art. The memory device 47 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disc (CD), digital versatile disc (DVD), . . . ), smart cards, flash memory devices, etc. The data visualization device 45 may have one or more computer-readable media that use the same or a different memory media technology. Data visualization device also may have one or more drives that support the loading of a memory media such as a CD, DVD, an external hard drive, etc. One or more external hard drives further may be connected to data visualization device using the communication interface.

As explained in the earlier sections, the processor 35 executes instructions as understood by those skilled in the art. The instructions may be carried out by a special purpose computer, logic circuits, or hardware circuits. Processor 35 may be implemented in hardware and/or firmware. Processor 35 executes an instruction, meaning it performs/controls the operations called for by that instruction. The term "execution" is the process of running an application or the carrying out of the operation called for by an instruction. The instructions may be written using one or more programming language, scripting language, assembly language, etc. Processor 35 operably couples with the input interface (e.g. keyboard 44, mouse 43), with output interface (e.g. display 49), with the communication interface (e.g. modem 41), and with memory device 47 to receive, to send, and to process information. Processor 35 may retrieve a set of instructions from a permanent memory device and copy the instructions in an executable form to a temporary memory device that is generally some form of RAM. Data visualization device 45 may also include a plurality of processors that use the same or a different processing technology.

A data visualization application in the form of program 48 may be provided on the data visualization device 45 to perform operations associated with providing one or more visualizations in the form of graphical displays such as graph 207, generated from datasets associated with water quality parameters (which encompasses monitoring sewage parameters in some embodiments) measured for each measurement event from the plurality of the water sampling sub-systems 100. Some or all of the operations described herein may be embodied in data visualization application 48. The operations may be implemented using hardware, firmware, software, or any combination of these methods. Referring to the example embodiment of FIG. 2, the data visualization method is implemented in software in the form of program 48 (comprised of computer-readable and/or computer-executable instructions) stored in the memory device 47 and accessible by processor 35 for execution of the instructions that embody the operations of data visualization application. Data visualization application 48 may be written using one or more programming languages, assembly languages, scripting languages, etc.

The data visualization application 48 may also be implemented as a Web application. For example, data visualization application may be configured to receive hypertext transport protocol (HTTP) responses and to send HTTP requests. The HTTP responses may include web pages such as hypertext markup language (HTML) documents and linked objects generated in response to the HTTP requests. Each web page may be identified by a uniform resource locator (URL) that includes the location or address of the computing device that contains the resource to be accessed in addition to the location of the resource on that computing device. The type of file or resource depends on the Internet application protocol such as the file transfer protocol, HTTP, H.323, etc. The file accessed may be a simple text file, an image the an audio file, a video file, an executable, a common gateway interface application, a Java applet, an extensible markup language (XML) file, or any other type of file supported by HTTP.

Each dataset visualized by se visualization device 45 according to an embodiment of the present invention includes measurement values for a plurality of water quality parameters undertaken by every connected water sampling sub-system 100 for a measurement event. For every measurement event, each water sampling sub-system 100 may undertake measurement of a plurality of water quality parameters at the same time (when a measurement event is triggered across all the water sampling sub-systems 100). For example, values for the following water quality parameters may be measured:

(a) pressure,
(b) transient pressure;
(b) temperature of water;
(c) pH of water;
(d) oxidation reduction potential (ORP);
(e) Conductivity (Ec)
(f) Free Chlorine concentration
(g) Turbidity Data generated by each water sampling sub-system 100 for each measurement event is logged in its Remote Terminal Unit (RTU) data logger 122 and may be transmitted to a central database 42. The database may also take the form of a computer-readable medium and/or on one or more other computing devices and accessed by the remote server computer 33 using the communication interface 41. The dataset may be stored using various file formats as known to those skilled in the art including a file, a file system, a relational database, a system of tables, a structured query language database, a cube, etc.

Referring to FIG. 3, and to FIG. 4 which is a detail of the first six hours of the graph displayed in FIG. 3, an example of the result of operations performed by the data visualizer 45 is illustrated. In the illustrated example, free chlorine levels were measured by each water sampling sub-system 100. A measurement event 213 was triggered across all of the water sampling sub-systems 100 every five minutes and measurements were recorded for a 7 day period. Free chlorine measurements were conducted for 1 week by using 16 sampling sub-systems where each sampling subs-system conducted 2,193 measurements (measurements every five minutes) over the 7 day period or 35,088 individual measurements were performed.

In a visualisation operation, a graph (similar to the graph 207 shown in FIG. 3) is presented by processor 35 on the display 49. The graph 207 includes a vertical axis 209 to indicate the maximum measured value (Mx) 2002, the minimum measured value (M N) 204 with the range 206 of the measured values of free chlorine being visually displayed on the graph 207. In addition, the average value 205 of free chlorine level across all 16-water sampling sub-systems 100 is also shown on the graph for each measurement event. The horizontal axis 211 indicates the time period over which a plurality of said measurement events have occurred thereby providing a visual indication of water quality. In the visualization shown in FIG. 3, the horizontal axis 211 is shown over a a 7-day time period.

Figure 5:
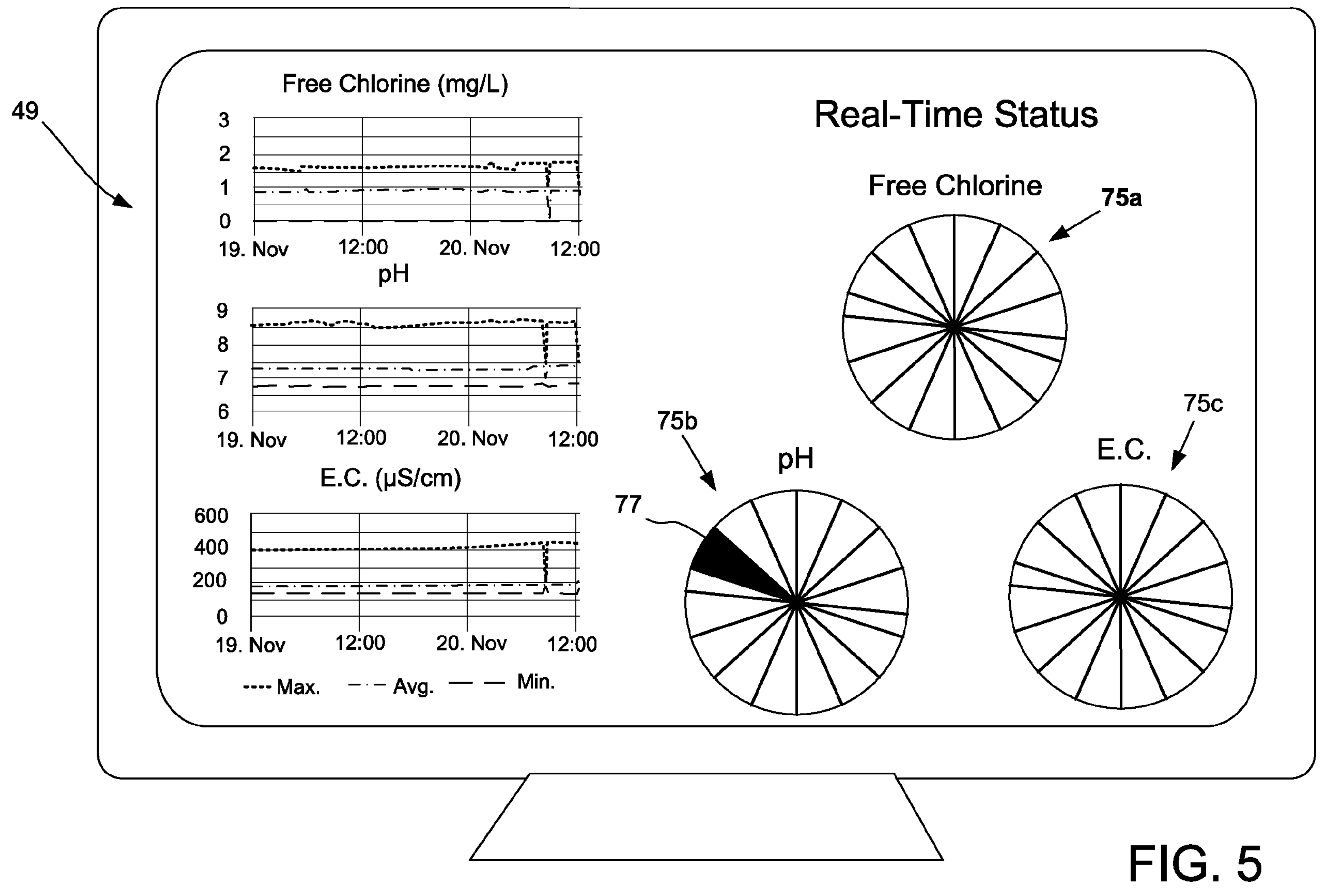

In the visualization operation, the memory device 47 may comprises executable instructions in program 48 for the processor 35 to compute the difference (a first variable) between the average value across all 16 sub-systems 100 for each measurement event and the maximum measured value or the minimum measured for each measurement. Similarly, deviation or difference (a second variable) between each individual value from the average value and the maximum and minimum values may also be computed. The first and second variable may then be processed in accordance with one or more predetermined rules to provide an indication of any unexpected changes in water quality. As shown in FIG. 5, when the pre-determined rules are satisfied, the data visualization device 45 provides an indication of the specific sub-system 100 which is recording unexpected changes in water quality. In the preferred embodiment, pie charts 75*a*, 75*b*, 75*c* have been shown with each sector of the pie chart denoting a specific water sampling sub-system 100. Any unexpected changes are indicated by red colour (represented in FIG. 5 by a black segment 77 in pie chart 75*b*) on the specific water sampling sub-system 100 when the predetermined rules are satisfied. The segments in a pie chart (may be identified as each segment representing a sensor sub-assembly 11) act as an immediate visual identifier of a node in the water distribution network 80 where some of the measured parameters lie above, or below, variable user pre-set or calculated defined limits for a measurement parameter.

In the example (shown in FIG. 5) for pH the red segment 77 is the highest grade of alarm indicating that pH at the site in question is well above, or below, the user established and pre-set alarm level parameters for maximum and minimum pH levels for that particular measurement node.

In some further embodiments, the segments of the pie charts may be programmed to provide more than one indication. For example, any segment may be shown as orange to signify that a measurement has exceeded a threshold alert level predetermined and set into the system by a user.

The segments in alert (orange) or alarm (red) status indicate real time events where water quality at the particular node is exceeding predetermined parameters of safe water quality established by the end user for that node, or part of a water distribution system.

It is important to note that even though the preferred embodiment utilizes a line graph, other graphs such as a bar graph, a histogram, a binned bar graph, a density plot graph, a kernel density estimation plot graph, a pie graph, a tree map, a bubble graph, etc. may be utilised without departing from the spirit and scope of the invention. Any graph where aggregated data is mapped to the dimensions of an element in the graph may be used.

The skilled reader will understand that the substance of the invention lies in the realisation that by triggering the sensor sub-assemblies to perform simultaneous (or near simultaneous) measurements at common measurement event times and then deriving average, minimum and range values from those measurements for parameters of interest, the measurements can be meaningfully presented to a human user in a manner that allows the user to quickly interpret the measurements and discern out of range measurements that may be a cause for alarm. Whilst the in the preferred embodiment a specially programmed computer has been used to implement the visualization.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

The invention claimed is:

1. A water quality monitoring system for monitoring water quality in a water distribution network comprising a plurality of distribution lines interconnecting one or more nodes from which water is supplied into the water distribution network, the water quality monitoring system comprising:

a plurality of water sampling sub-systems, each sub-system being arranged in fluid communication with a corresponding distribution line for obtaining water quality parameters from said corresponding distribution line, each sub-system comprising a communication module for communicating data related to a water quality parameter to a database over a communication network wherein each of the sub-systems are functionally linked with each other over the communication network to allow all of the sub-systems in the corresponding distribution lines for monitoring in an idle mode for a signal to ready itself to be triggered to perform simultaneous measurements of the water quality parameters in a measurement event;

a remotely located server computer in communication with said plurality of water sampling sub-systems, said server computer being in communication with a processor and a memory device, wherein said processor is operable to perform the steps of retrieving the data from the database to determine:

a maximum measured value for the water quality parameter from a set of water quality parameter values measured by each sub-system in each measurement event;

a minimum measured value for the water quality parameter from the set of water quality parameter values measured by each sub-system in each measurement event; and an average measured value for the water quality parameter computed by calculating an average of all measured values of the water quality parameter in the set;

wherein the memory device comprises executable instructions to configure the processor to display a graph, on a display device, that includes a first axis to indicate the maximum measured value, the minimum measured value and the average value for each measurement event and a second axis to indicate a time period over which a plurality of said measurement events have occurred thereby providing a visual indication of water quality, and wherein the memory device comprises executable instructions to compute at least one of: i) a difference average value of each and the minimum measured value for each measurement, and ii) a difference between an average value of each measurement and the maximum measured value for each measurement, and process the at least one computed difference in accordance with one or more predetermined rules to provide an indication of unexpected changes in water quality.

2. A water quality monitoring system in accordance with claim 1, wherein the processor for the remotely located server computer is operable to determine a range of the measured values of the water quality parameter by computing a difference between the maximum measured value and the minimum measured value and wherein the memory device comprises executable instructions to indicate the range of the measured values on the first axis.

3. A water quality monitoring system in accordance with claim 1 further comprising a user input interface in communication with the processor for controlling operation of the water sampling sub-systems and initiating one or more measurement events in a time period.

4. A water quality monitoring system in accordance with claim 1 wherein each sub-system is configured to measure one or more of the following:

(a) pressure;
(b) transient pressure;
(c) temperature of water;
(d) pH of water;
(e) oxidation reduction potential (ORP);
(e) Conductivity (Ec); and
(f) Free Chlorine concentration
(g) Turbidity.

5. A water quality monitoring system in accordance with claim 1 wherein the memory device comprises executable instructions to additionally display pre-determined maximum and minimum limit values for the water quality parameter.

6. A water quality monitoring system in accordance with claim 1 wherein the memory device comprises executable instructions to process the measured value for each measurement in accordance with one or more predetermined rules to provide an indication of unexpected changes in water quality.

7. A method of monitoring water quality in a water distribution network comprising a plurality of distribution lines for interconnecting a plurality of distribution lines with one or more nodes from which water is supplied into the water distribution network, the method comprising:

arranging a plurality of water sampling sub-systems in fluid communication with a corresponding distribution line and obtaining water quality parameters from said corresponding distribution line wherein each of the sub-systems functionally linked with each other over the communication network to allow all of the sub-systems in the corresponding distribution lines for monitoring in an idle mode for a signal received wirelessly to ready itself to be triggered to perform simultaneous measurements of the water quality parameters in a measurement event;

communicating data, via the communication module of the water sampling sub-system, related to a water quality parameter to a database over a communication network;

arranging a remotely located server computer and retrieving data from the database, said server computer being in communication with a processor and a non-volatile memory device and operating the processor to process the retrieved data to determine:

a maximum measured value for the water quality parameter from a set of water quality parameter values measured by each sub-system in each measurement event;

a minimum measured value for the water quality parameter from the set of water quality parameter values measured by each sub-system in each measurement event;

an average measured value for the water quality parameter computed by calculating an average of all the measured values of the water quality parameter in the set; and arranging a display device in communication with the processor and the memory device to display a graph that includes a first axis to indicate the maximum measured value, the minimum measured value and the average value for each measurement event and a second axis to indicate a time period over which a plurality of said measurement events have occurred to thereby provide a visual indication of water quality, and computing at least one of: i) a difference between value of each measurement and the maximum measured value for each measurement, and ii) a difference between an average value of each measurement and the minimum measured value for each measurement and processing said at least one computed difference in accordance with one or more predetermined rules to provide an indication of unexpected changes in water quality.

8. A method in accordance with claim 7 further comprising the step of determining a range of the measured values of the water quality parameter by computing a difference between the maximum measured value and the minimum measured value and wherein the memory device comprises executable instructions to indicate the range of measured values on the first axis.

9. A method in accordance with claim 7 comprising measuring one or more of the following water quality parameters:

each sub-system is configured to measure one or more of the following:

(a) pressure;
(b) transient pressure;
(c) temperature of water;
(d) pH of water;
(e) oxidation reduction potential (ORP);
(f) Conductivity (Ec); and
(g) Free Chlorine concentration
(h) Turbidity.

10. A method in accordance with claim 7 further comprising the step of displaying pre-determined maximum and minimum limit values for the water quality parameter on the display device.

* * * * *